(12) United States Patent
Nycz et al.

(10) Patent No.: US 8,137,277 B2
(45) Date of Patent: Mar. 20, 2012

(54) VOLUMETRIC MEASUREMENT AND VISUAL FEEDBACK OF TISSUES

(75) Inventors: Jeffrey H. Nycz, Warsaw, IN (US); Carlos E. Gil, Collierville, TN (US); William T. Donofrio, Andover, MI (US); Jeetendra Subhash Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/040,730

(22) Filed: Mar. 4, 2011

(65) Prior Publication Data

US 2011/0160587 A1 Jun. 30, 2011

Related U.S. Application Data

(62) Division of application No. 11/403,095, filed on Apr. 11, 2006, now Pat. No. 7,918,796.

(51) Int. Cl.
*A61B 8/00* (2006.01)

(52) U.S. Cl. ........ 600/439; 600/407; 600/410; 600/437; 600/417

(58) Field of Classification Search .................. 600/407, 600/410, 437, 417, 439
See application file for complete search history.

(56) References Cited

U.S. PATENT DOCUMENTS

| | | |
|---|---|---|
| 3,181,528 A | 5/1965 | Brackin |
| 4,080,653 A | 3/1978 | Barnes, Jr. et al. |
| 4,195,367 A | 4/1980 | Kraus |
| 4,195,643 A | 4/1980 | Pratt, Jr. |
| 4,246,791 A | 1/1981 | Glenn |
| 4,281,667 A | 8/1981 | Cosman |
| 4,407,296 A | 10/1983 | Anderson |
| 4,430,999 A | 2/1984 | Brighton et al. |
| 4,519,394 A | 5/1985 | Black et al. |
| 4,519,401 A | 5/1985 | Ko et al. |
| 4,669,482 A | 6/1987 | Ophir |
| 4,672,963 A | 6/1987 | Barken |
| 4,781,181 A | 11/1988 | Tanguy |
| 4,785,822 A | 11/1988 | Wallace |
| 4,813,435 A | 3/1989 | Arms |
| 4,846,191 A | 7/1989 | Brockway et al. |
| 4,993,428 A | 2/1991 | Arms |
| 5,038,787 A | 8/1991 | Antich et al. |
| 5,083,573 A | 1/1992 | Arms |
| 5,125,408 A | 6/1992 | Basser |
| 5,178,148 A | 1/1993 | Lacoste et al. |
| 5,188,109 A | 2/1993 | Saito |
| 5,197,475 A | 3/1993 | Antich et al. |
| 5,306,306 A | 4/1994 | Bisek et al. |
| 5,360,016 A | 11/1994 | Kovacevic |
| 5,394,875 A | 3/1995 | Lewis et al. |
| 5,402,781 A | 4/1995 | Dimarogonas |
| 5,413,116 A | 5/1995 | Radke et al. |
| 5,425,775 A | 6/1995 | Kovacevic et al. |
| 5,456,724 A | 10/1995 | Yen et al. |
| 5,470,354 A | 11/1995 | Hershberger et al. |

(Continued)

FOREIGN PATENT DOCUMENTS

DE 10342823 A1 4/2005

(Continued)

*Primary Examiner* — Brian Casler
*Assistant Examiner* — Joel Lamprecht

(57) ABSTRACT

Apparatus and methods for assessing tissue characteristics such as the dimensions and volume of an osteolytic lesion are disclosed. The apparatus may utilize ultrasound to provide visual and volumetric feedback related to a lesion or other tissue. Further the apparatus may be utilized to determine whether the lesion has been completely removed and filled with the appropriate amount of graft material.

20 Claims, 2 Drawing Sheets

U.S. PATENT DOCUMENTS

| | | |
|---|---|---|
| 5,480,439 A | 1/1996 | Bisek et al. |
| 5,533,519 A | 7/1996 | Radke et al. |
| 5,535,752 A | 7/1996 | Halperin et al. |
| 5,564,423 A | 10/1996 | Mele et al. |
| 5,564,434 A | 10/1996 | Halperin et al. |
| 5,590,658 A | 1/1997 | Chiang et al. |
| 5,651,767 A | 7/1997 | Schulman et al. |
| 5,690,114 A | 11/1997 | Chiang et al. |
| 5,695,496 A | 12/1997 | Orsak et al. |
| 5,720,771 A | 2/1998 | Snell |
| 5,749,363 A | 5/1998 | Ishii et al. |
| 5,759,199 A | 6/1998 | Snell et al. |
| 5,810,735 A | 9/1998 | Halperin et al. |
| 5,836,876 A | 11/1998 | Dimarogonas |
| 5,839,442 A | 11/1998 | Chiang et al. |
| 5,852,647 A | 12/1998 | Schick et al. |
| 5,891,033 A | 4/1999 | O'Neill et al. |
| 5,935,171 A | 8/1999 | Schneider et al. |
| 5,938,610 A | 8/1999 | Ohtomo |
| 5,957,846 A | 9/1999 | Chiang et al. |
| 5,964,709 A | 10/1999 | Chiang et al. |
| 5,984,875 A | 11/1999 | Brune |
| 5,993,395 A | 11/1999 | Shulze |
| 6,034,296 A | 3/2000 | Elvin et al. |
| 6,059,784 A | 5/2000 | Perusek |
| 6,074,394 A | 6/2000 | Krause |
| 6,106,472 A | 8/2000 | Chiang et al. |
| 6,125,290 A | 9/2000 | Miesel |
| 6,144,866 A | 11/2000 | Miesel et al. |
| 6,171,252 B1 | 1/2001 | Roberts |
| 6,185,452 B1 | 2/2001 | Schulman et al. |
| 6,200,266 B1 | 3/2001 | Shokrollahi et al. |
| 6,208,894 B1 | 3/2001 | Schulman et al. |
| 6,221,024 B1 | 4/2001 | Miesel |
| 6,223,081 B1 | 4/2001 | Kerver |
| 6,230,036 B1 | 5/2001 | O'Neill et al. |
| 6,235,038 B1 | 5/2001 | Hunter et al. |
| 6,241,673 B1 | 6/2001 | Williams |
| 6,245,109 B1 | 6/2001 | Mendes et al. |
| 6,248,080 B1 | 6/2001 | Miesel et al. |
| 6,285,897 B1 | 9/2001 | Kilcoyne et al. |
| 6,364,849 B1 | 4/2002 | Wilcox |
| 6,433,629 B2 | 8/2002 | Hamel et al. |
| 6,436,042 B1 | 8/2002 | Cadossi et al. |
| 6,447,448 B1 | 9/2002 | Ishikawa et al. |
| 6,450,946 B1 | 9/2002 | Forsell |
| 6,454,699 B1 | 9/2002 | Forsell |
| 6,454,700 B1 | 9/2002 | Forsell |
| 6,503,249 B1 | 1/2003 | Krause |
| 6,529,127 B2 | 3/2003 | Townsend et al. |
| 6,540,685 B1 | 4/2003 | Rhoads et al. |
| 6,544,749 B1 | 4/2003 | Kim |
| 6,546,268 B1 | 4/2003 | Ishikawa et al. |
| 6,573,706 B2 | 6/2003 | Mendes et al. |
| 6,582,365 B1 | 6/2003 | Hines et al. |
| 6,583,630 B2 | 6/2003 | Mendes et al. |
| 6,585,647 B1 | 7/2003 | Winder |
| 6,610,096 B2 | 8/2003 | MacDonald |
| 6,615,067 B2 | 9/2003 | Hoek et al. |
| 6,638,231 B2 | 10/2003 | Govari et al. |
| 6,656,135 B2 | 12/2003 | Zogbi et al. |
| 6,676,291 B2 | 1/2004 | Ahn |
| 6,689,056 B1 | 2/2004 | Kilcoyne et al. |
| 6,692,450 B1 | 2/2004 | Coleman |
| 6,695,885 B2 | 2/2004 | Schulman et al. |
| 6,706,005 B2 | 3/2004 | Roy et al. |
| 6,712,772 B2 | 3/2004 | Cohen et al. |
| 6,714,763 B2 | 3/2004 | Hamel et al. |
| 6,733,458 B1 | 5/2004 | Steins et al. |
| 6,761,741 B2 | 7/2004 | Iesaka |
| 6,783,499 B2 | 8/2004 | Schwartz |
| 6,802,811 B1 | 10/2004 | Slepian |
| 6,821,299 B2 | 11/2004 | Kirking et al. |
| 6,846,288 B2 | 1/2005 | Nagar et al. |
| 6,849,463 B2 | 2/2005 | Santini, Jr. et al. |
| 6,889,165 B2 | 5/2005 | Lind et al. |
| 6,899,680 B2 | 5/2005 | Hoff et al. |
| 6,980,419 B2 | 12/2005 | Smith et al. |
| 6,988,991 B2 | 1/2006 | Kim et al. |
| 7,004,904 B2 | 2/2006 | Chalana et al. |
| 7,006,955 B2 | 2/2006 | Daft et al. |
| 7,025,725 B2 | 4/2006 | Dione et al. |
| 7,041,059 B2 | 5/2006 | Chalana et al. |
| 7,044,912 B2 | 5/2006 | Babu et al. |
| 7,052,461 B2 | 5/2006 | Willis |
| 7,063,666 B2 | 6/2006 | Weng et al. |
| 7,232,416 B2 | 6/2007 | Czernicki |
| 2002/0049394 A1 | 4/2002 | Roy et al. |
| 2002/0099288 A1 | 7/2002 | Chang et al. |
| 2002/0103435 A1 | 8/2002 | Mault |
| 2002/0107649 A1 | 8/2002 | Takiguchi et al. |
| 2002/0133094 A1 | 9/2002 | Wilcox et al. |
| 2002/0151894 A1 | 10/2002 | Melkent et al. |
| 2002/0198526 A1 | 12/2002 | Shaolian et al. |
| 2003/0032874 A1 | 2/2003 | Rhodes et al. |
| 2003/0069644 A1 | 4/2003 | Kovacevic et al. |
| 2003/0105470 A1 | 6/2003 | White |
| 2003/0139690 A1 | 7/2003 | Aebli et al. |
| 2003/0167002 A1 | 9/2003 | Nagar et al. |
| 2003/0186914 A1 | 10/2003 | Hofer et al. |
| 2004/0011671 A1 | 1/2004 | Shults et al. |
| 2004/0054302 A1 | 3/2004 | Czernicki |
| 2004/0059423 A1 | 3/2004 | Barnes et al. |
| 2004/0136221 A1 | 7/2004 | Iwasaki |
| 2004/0143186 A1 | 7/2004 | Anisimov et al. |
| 2004/0143302 A1 | 7/2004 | Sieracki et al. |
| 2004/0176672 A1 | 9/2004 | Silver et al. |
| 2004/0197267 A1 | 10/2004 | Black et al. |
| 2004/0204744 A1 | 10/2004 | Penner et al. |
| 2004/0230115 A1 | 11/2004 | Scarantino et al. |
| 2004/0236192 A1 | 11/2004 | Necola Shehada et al. |
| 2004/0236221 A1 | 11/2004 | Wilcox et al. |
| 2005/0010299 A1 | 1/2005 | DiSilvestro |
| 2005/0010300 A1 | 1/2005 | DiSilvestro et al. |
| 2005/0010301 A1 | 1/2005 | DiSilvestro et al. |
| 2005/0010302 A1 | 1/2005 | Dietz et al. |
| 2005/0012610 A1 | 1/2005 | Liao et al. |
| 2005/0012617 A1 | 1/2005 | DiSilvestro et al. |
| 2005/0015010 A1 | 1/2005 | Antich et al. |
| 2005/0085725 A1 | 4/2005 | Nagar et al. |
| 2005/0103625 A1 | 5/2005 | Rhodes et al. |
| 2005/0107677 A1 | 5/2005 | Ward et al. |
| 2005/0113691 A1 | 5/2005 | Liebschner |
| 2005/0119587 A1 | 6/2005 | Roessler et al. |
| 2005/0124873 A1 | 6/2005 | Shults et al. |
| 2005/0197576 A1 | 9/2005 | Luo et al. |
| 2005/0228247 A1 | 10/2005 | Scarantino et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2007/0179568 A1 | 8/2007 | Nycz et al. |
| 2007/0197895 A1 | 8/2007 | Nycz et al. |
| 2007/0232958 A1 | 10/2007 | Donofrio et al. |

FOREIGN PATENT DOCUMENTS

| | | |
|---|---|---|
| EP | 0344770 A1 | 12/1989 |
| EP | 0423420 A2 | 4/1991 |
| EP | 1238630 A2 | 9/2002 |
| EP | 1285640 A2 | 2/2003 |
| EP | 1442715 A2 | 8/2004 |
| WO | 8911244 A1 | 11/1989 |
| WO | 9217113 A1 | 10/1992 |
| WO | 9733513 A1 | 9/1997 |
| WO | 0215769 A2 | 2/2002 |
| WO | 0230338 A1 | 4/2002 |
| WO | 02085193 A2 | 10/2002 |
| WO | 2005007025 A2 | 1/2005 |
| WO | 2006105098 A2 | 10/2006 |

US 8,137,277 B2

VOLUMETRIC MEASUREMENT AND VISUAL FEEDBACK OF TISSUES

CROSS REFERENCE TO RELATED APPLICATION

This application is a divisional application of U.S. patent application Ser. No. 11/403,095, filed Apr. 11, 2006.

TECHNICAL FIELD

The present disclosure is directed to improved instrumentation and methods for assessing characteristics of a tissue. More particularly, in one aspect the present disclosure is directed toward instruments and methods for assessing characteristics of a lesion.

BACKGROUND

The present disclosure relates to the assessment of various characteristics of tissues, including the size and dimensions of osteolytic lesions. Joint prostheses often include an articulating surface composed of a material designed to minimize the friction between components of the joint prostheses. For example, in a hip prosthesis the femoral component is comprised of a head (or ball) and a stem attached to the femur. The acetabular component is comprised of a cup (or socket) attached to the acetabulum and most often includes a polyethylene articulating surface. The ball-in-socket motion between the femoral head and the acetabular cup simulates the natural motion of the hip joint and the polyethylene surface helps to minimize friction during articulation of the ball and socket. However, this articulation has been shown to release submicron particle wear debris, often polyethylene wear debris. The release of this debris into the body has been shown to lead to the development of osteolytic lesions.

Current techniques for treating lytic and cancerous lesions include debriding the lesion and filling the remaining defect with graft materials. Currently surgeons lack a convenient and accurate way to confirm the exact location of the lesion, whether the lesion has been completely removed, and whether the remaining void has been properly filled with graft material. Further, advanced treatment options use osteoinductive and osteoconductive materials to heal the lesion. These materials require an accurate assessment of the volume and shape of the lesion to ensure that the appropriate amount of biological agent is introduced into the lesion to promote rapid bone growth and healing.

Therefore, there remains a need for improved instruments and methods of evaluating characteristics of tissue and, in particular, bone lesions.

SUMMARY

In one embodiment, a system for determining a characteristic of a lesion of a bone is provided. The system includes a hand-held ultrasound device for detecting indicators of a lesion, a processor for determining a characteristic of the lesion based on the detected indicators, and a display for displaying a representation of the characteristic. In one aspect, a coupling attachment is provided to enable effective conductive coupling between the ultrasound device and the bone.

In another embodiment, a method of treating a lesion of a bone is provided. The method includes providing an ultrasound device, a processor, and a display. The method includes sensing the signals of the ultrasound device reflected from the bone and lesion, determining a lesion model based on the sensed signals, and displaying at least one characteristic of the lesion model.

Further aspects, forms, embodiments, objects, features, benefits, and advantages of the present invention shall become apparent from the detailed drawings and descriptions provided herein.

DESCRIPTION

Figure 1:
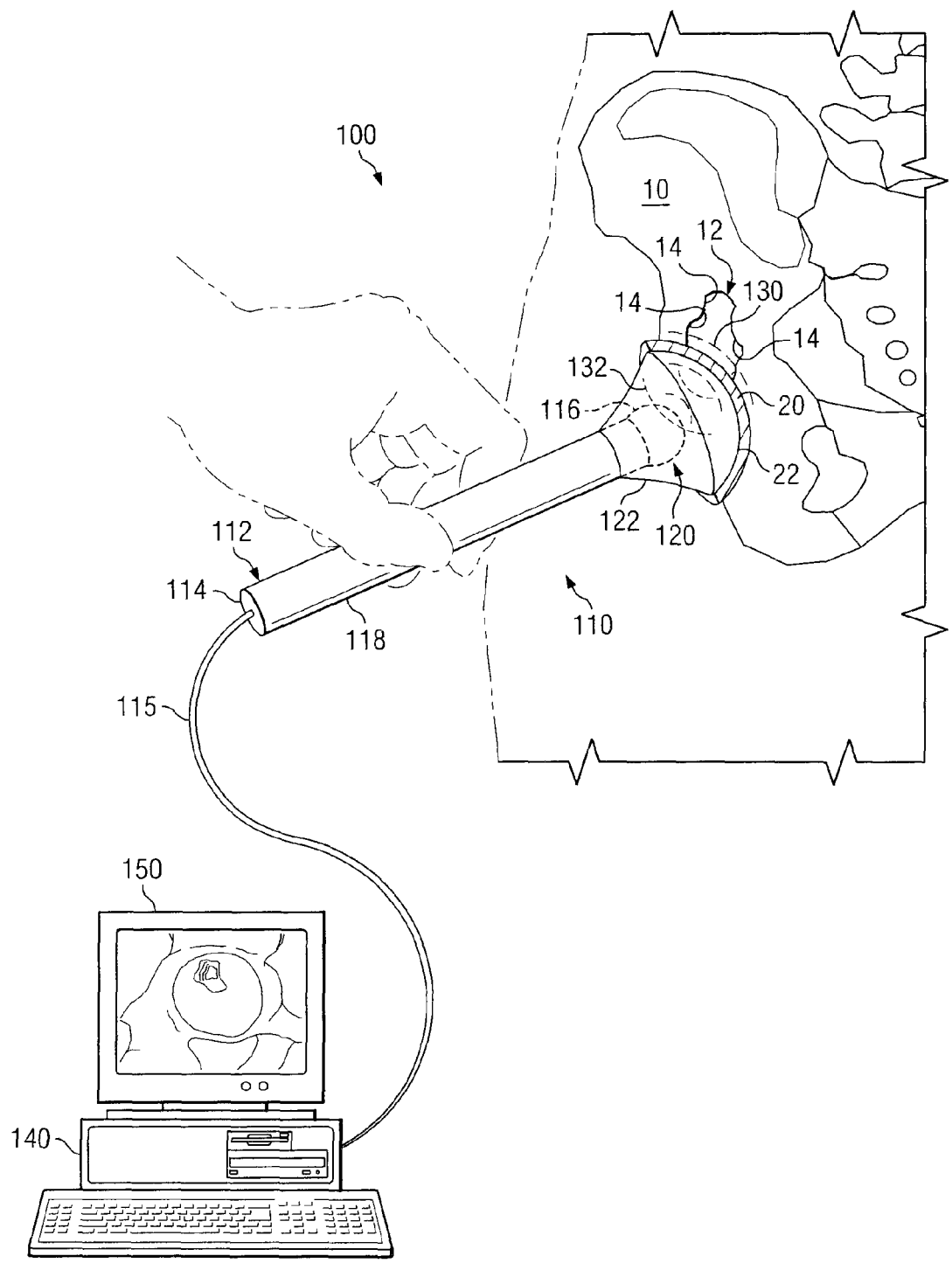
FIG. 1 is a front view of one embodiment of a system for determining a characteristic of a lesion of a bone in use with an artificial acetabular cup.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates.

Figure 2:
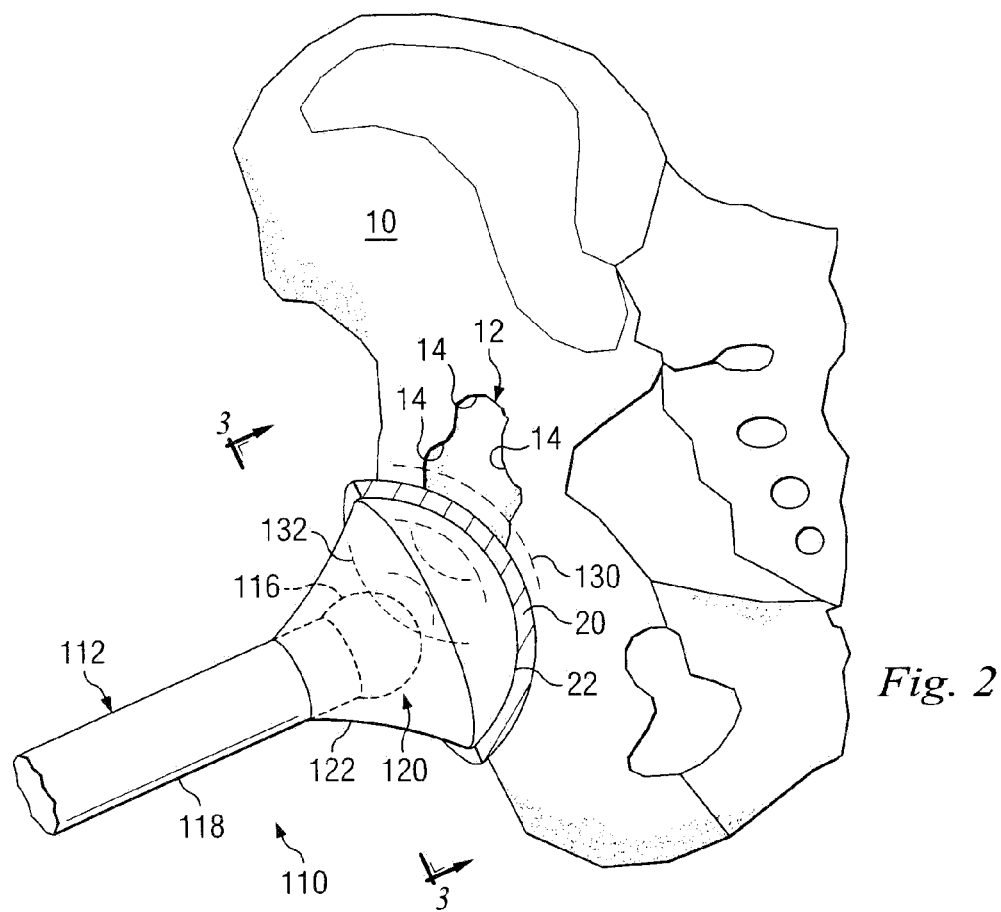
FIG. 2 is an enlarged front view of a portion of FIG. 1.
Figure 3:
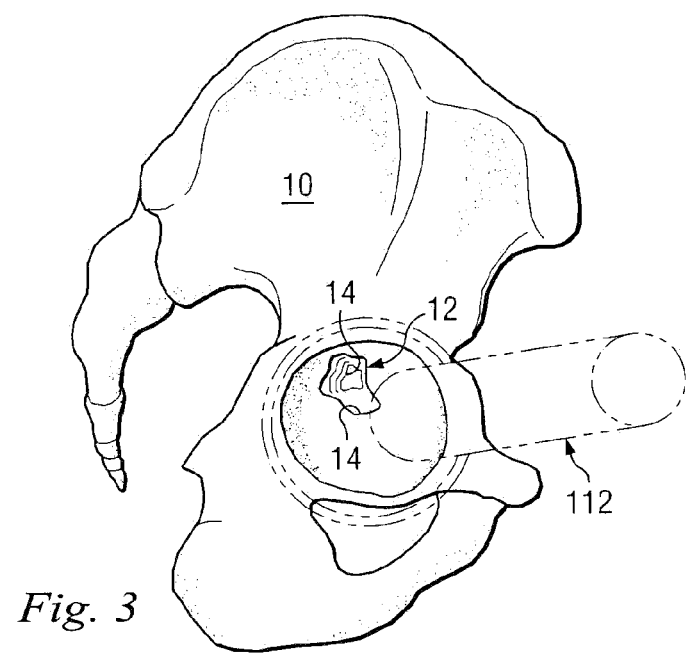
FIG. 3 is an enlarged side view of a portion of FIG. 1.

Referring now to FIGS. 1-3, there is shown a system 100 for assessing the volume and dimensions of an osteolytic lesion. FIG. 1 shows the system 100 being utilized to assess an osteolytic lesion 12 of a patient's acetabulum 10 where the patient has an artificial hip prosthesis. The hip prosthesis includes an artificial acetabular cup 20. The system 100 includes a hand-held ultrasonic device 110, a processor 140, and a display 150. Although shown separately, the processor may be incorporated into the hand-held device 110, the display 150, or be a stand alone unit. For example, in one embodiment the display and the processor are parts of a desk top computer or similar device. Further, in some embodiments, the display 150 is incorporated into the hand-held device 110. Thus, in at least one embodiment the system 100 consists of a hand-held device that incorporates both the processor 140 and the display 150. Examples of similar systems are disclosed in U.S. patent application filed Feb. 17, 2006 as Ser. No. 11/356,643 entitled "Surgical Instrument to Assess Tissue Characteristics," and Ser. No. 11/356,687 entitled "Sensor and Method for Spinal Monitoring," that are herein incorporated by reference in their entirety.

The hand-held device 110 has a body 112, a proximal end 114, a distal end 116 and a cable 115 connecting the device to the processor 140. In FIG. 1, the body 112 is shown as being substantially cylindrical and elongated. This is merely for illustrative purposes. The body 112 may take any shape, including non-cylindrical and non-elongated designs, capable of holding the electrical and mechanical components of the hand-held device 100. The body 112 includes a gripping surface 118 for grasping by the user or engagement with another instrument. The gripping surface 118 may include protrusions, recesses, or other features to facilitate engagement with another instrument. In one embodiment the gripping surface 118 is disposed closer to the proximal end 114 than to the distal end 116. A transmitter 120 is disposed adjacent the distal end 116.

In some embodiments the transmitter 120 is an ultrasound device. In that regard, the transmitter 120 is adapted to provide information or data to the processor 140 through cable 115 that may be processed to create 3 dimensional ("3-D") models and volumetric data related to osteolytic lesion 10 using ultrasound. In some embodiments the transmitter 120 is adapted to produce ultrasound waves that will pass through a portion of an artificial implant, such as the acetabular cup 20. In one embodiment, the transmitter 120 consists of an acoustic transducer that is adapted for emitting acoustic signals and detecting the reflected acoustic signals. The acoustic transducer may function as a pulse-echo transducer having a single element for emitting and receiving acoustic signals. The transmitter 120 includes an energy source for producing or emitting the acoustic or ultrasound signal and a sensor for detecting the echo or reflected signal. In one embodiment, the functions of the energy source and the sensor are performed by a single component switched between a transmit mode and a listen mode. In another embodiment, the transmitter 120 includes two components. The first component is configured for emitting signals and a second component is configured to receive or detect the returned signals.

It is to be understood that ultrasound is a form of transmitted energy. In alternative embodiments other forms of energy and different frequencies are used, such as other types of acoustics, lasers, visible light, radio frequency, microwaves, etc., provided they can be transmitted into the lesion and/or tissue. For instance, the signals disclosed in the present embodiment are in the frequency range of ultrasonic signals. In some high resolution systems of the present disclosure, the frequency can range from 20 KHz up to and exceeding 300 MHz. For example, these frequencies may be used in acoustic microscopic instrument applications. In one aspect of the present disclosure, the frequency range is between 1 MHz to 15 MHz. Still further, the energy source may be any source capable of transmitting energy into the affected region to obtain characteristics of the tissue. For example, in some embodiments the energy source utilizes RF energy in the range from 400 KHz up to 10 GHz. Still further, in some embodiments the energy source utilizes a light source generating non-coherent light, coherent (laser) light, or a combination of the two.

The strength and frequency of the signal can be varied depending on the type of tissue being evaluated. Further, the strength and frequency of the signal may be varied to enhance the accuracy of evaluation of a lesion boundary. For instance, in one aspect the system 100 evaluates the lesion void with multiple energy beams with different frequencies and then integrates or combines the sensed signal information utilizing the processor to best approximate the size and location of the void. Further, in another aspect the energy beam or signal is shaped for optimum performance and in some embodiments are focused beams, such as beams with a substantially cylindrical or conical shape. As shown in FIGS. 2 and 3, the osteolytic lesion 12 may have an irregular boundary 14 between the good bone and the lesion. In still another aspect, the signal is adapted to precisely detect the contours of the boundary 14. This is accomplished by such means as using a phased array of transducers, utilizing fiducial markers in combination with the signals, or any other suitable means. In an additional embodiment, one or more secondary or ancillary acoustic energy sources separate from the transmitter 120 are applied to the body near the boney area of interest. The energy transmitted by these secondary sources passes through or reflects from the bone and lesion and is sensed by the transmitter 120. This additional information is included in the data used to create a 3-D model representative of at least a portion of a lesion.

To increase the efficiency and accuracy of the transmitter 120, and in particular the transmission of signals into the tissue, the distal end 116 of the hand-held device 110 is shaped to substantially match the contours of a surface of the tissue or a corresponding implant such that the hand-held device and the tissue or implant are in conductive contact. That is, the hand-held device and implant are in sufficient conductive contact, not necessarily direct contact, to facilitate transmission of energy signals into the osteolytic lesion and surrounding tissue. In one embodiment, the exterior of the distal end 116 of the hand-held device 110 is adapted to selectively engage a coupling attachment 122 formed of an ultrasonic conductive material that is shaped to mate with the acetabular cup 20, as shown in FIG. 1. The coupling attachment 122 has an internal cavity adapted to receive at least a portion of distal end 116. This internal cavity may have a fixed geometry or may include a malleable material such as an elastomeric material such that the internal cavity can conform to different sizes and shapes of distal ends 116 on the hand-held device as may occur from different manufacturers. Further, in another aspect the system 100 includes a plurality of coupling attachments 122 having different shapes and sizes corresponding to different types and sizes of acetabular cups to effectively transmit acoustic energy through the coupler while generating few, if any, unwanted artifacts. The appropriate shape and size of coupling attachment 122 is chosen based on the patient and/or the size of the artificial implant. In a further aspect, a series of coupling attachments 122 are shaped to precisely mate with a specific type model of acetabular cup from a specific manufacturer. A series of coupling attachments 122 is provided to match-up with more than one model of acetabular cup, including those made by different manufacturers. Further, although the illustrated implant appears to have a substantially uniform curvature, it is contemplated that in alternative embodiments the coupling attachment will have an asymmetrical form to match a similar asymmetrical form on the implant.

In some embodiments the coupling attachment 122 is at least partially malleable to facilitate more intimate coupling with the implant or tissue of the patient by conforming to the surface. The malleable material may be a moldable putty type material, an elastomeric material such as PORON® foam or silicon, a gel or other suitable materials. Thus, the coupling attachment 122 need not always be specifically designed to match a particular implant. Rather, in these embodiments the coupling attachment 122 has at least an external surface that is malleable to mate with numerous implants of different shapes and sizes. In a further embodiment, a coupling fluid (not shown) is provided between the coupling attachment 122 and the artificial implant. In this form, the coupling attachment 122 is in enhanced conductive communication with the implant via a coupling fluid. The coupling fluid may be used to increase the efficiency of the transmission of energy signals, including ultrasound, from the instrument through the implant and into the bone. Also, in some embodiments the distal end 116 itself of the hand-held device 110 is shaped to match the corresponding surface without the need for a coupling attachment.

The coupling attachment 122 is adapted for placement at the distal end 116 such that when the system 100 is in use the hand-held unit 100 can emit a signal or other type of energy wave into the tissue being monitored and receive an echo or return signal. To this end, in one embodiment, the coupling attachment 122 includes a conductive surface. Conductive surface in this context does not require, but may include electrical conductivity. Conductive surface in this context is intended to mean a surface configured to facilitate the emitting and receiving of the ultrasound or other energy signals. Thus, the surface may serve as a transducer to emit the signals or receive the signals, or the surface may simply be transmissive allowing the signals to pass through. In some embodiments, the acetabular cup 20 or other artificial implant is utilized as the conductive surface to facilitate transmission of the signals into the tissue. In this way, the acetabular cup 20 is a part of the system 100 in some embodiments. That is, in some embodiments the hand-held device 110 is coupled to the acetabular cup 20 via coupling attachment 122 such that the acetabular cup is utilized to transmit and receive the signals. Other types of implants besides acetabular cups may be used to transmit and receive the signals. In some embodiments, the signals merely pass through the acetabular cup 20.

Consider the case of an osteolytic lesion 12 of the acetabulum 10, as shown in FIGS. 1 and 2. An appropriately sized coupling attachment 122 is mounted on distal end 116 and is placed in conductive contact with a surface 22 of the artificial acetabular cup 20. Conductive contact implies that the coupling attachment 122 and, therefore, the transmitter 120 of the hand-held device 110 are in sufficient contact, either direct or indirect, with the acetabular cup 20 to emit a signal or beam into the lesion and receive a reflected signal from a boundary 14 between the lesion and the healthy bone of the acetabulum 10. As discussed above, in some embodiments the acetabular cup 20 facilitates the emission or receiving of signals. In other embodiments, the signals merely pass through the acetabular cup 20. In one aspect, the coupling attachment 122 is adapted for conductive contact with the acetabular cup 20 using a coupling medium, such as coupling liquid or other substance. In another aspect, the coupling attachment 122 is adapted for direct contact with the lesion 12 after removal of the artificial acetabular cup 20. Further, in some embodiments the transmitter 120 is adapted for direct contact with the acetabular cup 20 or the lesion 12. In other embodiments, particularly where the osteolytic lesion 12 or other tissue feature is located within the acetabulum 10 or other tissue, the coupling attachment 122 is formed from an appropriate material and shaped to pierce through a portion of the acetabulum to become in direct conductive contact with the osteolytic lesion 20 as shown more fully in U.S. patent application Ser. No. 11/356,687 filed Feb. 17, 2006 incorporated herein by reference.

The transmitter 120 emits an ultrasound signal 130 into the osteolytic lesion 12 through coupling attachment 122 and the acetabular cup 20. The ultrasound signal 130 will pass through the lesion 12 until it arrives at the interface between the lesion and healthy bone, illustrated by boundary 14. At that point, a portion of the ultrasound signal 130 will reflect off of the boundary 14. This reflected signal is the echo or return signal 132 that will be received by the system 100 for determining the characteristics of the lesion, including size, volume and shape. In one embodiment, based on the time delay of the return signal 132 and the assumed constant speed of the acoustic signal in the lesion, the depth of the osteolytic lesion 12 at various points may be determined by the signal processor. This can be utilized to determine the shape and position of the lesion 12. The signal processor may also utilize this information to determine the volume of the lesion 20. It should be noted that determining volumetric measurements are intended to include approximations and estimations of the actual volume as well as precise determinations of volume. Further, the volume estimation may be based on the corresponding amount of bone filler required to fill the void once the lesion is removed, such as a small INFUSE® bone graft kit from Medtronic, Inc. or other similar bone growth stimulators, rather than a numerical representation, such as 36 cc.

The reflected signals 132 are used by the signal processor to determine the boundary of the lesion and to determine the volume based on the points defining the lesion boundary. In one embodiment, the boundaries are compared to one or more known geometric shapes of known volume to determine the best fit and thereby determine the best approximation of the volume of the lesion. For example, but without limitation to other shapes, the geometric shapes include spheres, cylinders, cubes, pyramids and cones. Further, more than one shape of different sizes may be used to approximate the lesion shape and volume. For example, a series of small cubes may be stacked in virtual space within the void boundaries to closely approximate the actual sensed volume. In one embodiment, the volume determination is made by the surgeon based upon the boundaries of the lesion. In another embodiment, the signal processor calculates both the boundaries and the volume of the lesion 12.

In some embodiments the transmitter 120 first emits a broad signal that travels into a wide area of the acetabulum 10. Then based upon the reflected signal from the broad signal, a narrower signal is focused upon an area where indicators of an osteolytic lesion were detected. This process is iterated until a beam of appropriate size is transmitted to detect the features of the osteolytic lesion. Where multiple lesions are detected the signal may focus upon one lesion at a time, repeating the process for the additional lesions after obtaining features of the first lesion. Focusing the signal on a specific location may be automatically performed based on calculations performed by the signal processor, manually performed by the operator, or a combination of the two. For example, the operator may utilize a 3-D display, discussed below, to identify generally the presence of a lesion and then focus the signal to obtain more information about the lesion such as its size, shape, and density. In these ways, the system 100 may focus in on the osteolytic lesion to obtain the most precise data and information available. Further, in other aspects, the user moves the location of transducer 120 to various points in three dimensional space and the processor determines volume and boundaries of the lesion based on the difference in reflected signals from the plurality of locations. In a further embodiment, the user applies a compressive force to the hand held probe that is transmitted to the bone and the lesion. A first ultrasonic reading is taken with the hand held probe or other tool compressing the bone and/or lesion with a first pressure. A second ultrasonic reading is taken with the hand held probe or other tool compressing the bone and/or lesion with a second pressure. The first and second ultrasonic readings are compared and the difference in the sensed characteristics under varying pressure is utilized to create at least a portion of a 3-D model representing the lesion. In still a further embodiment, a plurality of coupling attachments are provided with different surface contact areas. The user initial starts with a large surface contact coupler for the general ultrasonic survey of the area of interest. The user then selects a coupler having a smaller surface contact area, much less than the surface area of the implant such as shown in FIG. 1, and applies the coupler to the area of interest. If still further more detailed information is desired, a still smaller contact surface area coupler may be attached to the hand held probe and utilized to interrogate the lesion.

In some embodiments, the system 100 is used to create a 3-D image or model of the osteolytic lesion and surrounding bone from which the lesion may then be evacuated. The 3-D image may be viewed by the surgeon on the display 150. A second reading may be taken after debridement of the lesion. Then, based on the second reading, any remaining lesion may be identified and removed. In this way, the system 100 not only allows the physician to determine if any lesion remains, but also know precisely where any unwanted tissue remains.

This process can be iterated until the lesion is completely removed. This process allows for successful removal of all of the undesirable tissue, which in the case of osteolytic lesions has been difficult to determine in the past.

Where the electronic instrumentation 100 is utilized to check for the complete removal of the lesion 20 after debridement, a coupling media or filler material is used to fill the void. For example, in one embodiment the void is filled with a saline solution or other conductive substance such that the electronic instrumentation 100 may detect the boundaries between the saline and the lesion 20 to determine if the lesion has been fully removed. In one embodiment, the coupling media is a flowable material with known acoustic properties that are easily distinguishable from the lysis and surrounding bone. For example, but without limitation to other materials, the coupling media includes saline solution, blood, plasma, bone paste, bone wax, allograft, autograft, demineralized bone, BMP in a carrier matrix, mineralized granules, and bone cement. In an additional aspect, the system 100 is used to detect proper packing of the completely debrided void with bone filler material disposed between the bone filler material and the boney boundary. To this end the system may detect any remaining voids or the presence of foreign materials—such as the filler materials—in comparison to the original lesion.

Alternatively, for less defined lesion boundaries, reflected energy signals are processed to determine a gradient profile for the transitional tissue between the healthy bone and the homogenous lesion material to determine bone integrity or condition. Information from the reflected signals is used to by the health care provider to determine the extent of debridement desired for a successful procedure. In one embodiment, the system evaluates the boundary of the lesion to determine the gradient between the natural healthy tissue well outside the lesion, the substantially homogenous lesion material, and the transitional tissue of potentially compromised tissue extending between the lesion and the healthy tissue. In one form, the processor is programmed to select a debridement and volume boundary where the transitional tissue gradient is between 100% and 50% healthy tissue. In another form for cancerous lesion removal, the processor is programmed to set the debridement boundary so it includes a buffer of healthy tissue outside of the sensed lesion boundary to ensure that all of the cancerous and pre-cancerous cells are removed.

The system 100 includes a display 150. Depending on the type of data being obtained by the system 100 the display 150 may take on different forms. Where the system 100 is configured to create 3-D models of the tissue and lesion the display 150 must have sufficient resolution to show the details of the image. Thus, where 3-D images are utilized the display 150 may be a computer monitor, television, projector, or other display with sufficient output capabilities. In some embodiments, the system 100 will be adapted to create 2-D models of the tissue and the display 150 is adapted accordingly. In such cases, the 2-D images may be derived from the 3-D models. In some embodiments, views of a 3-D model will not be required and therefore the display 150 may have much lower resolution. For example, if the display 150 is adapted to show the estimated size of the lesion, such as "36 cc," a small liquid crystal display may be sufficient. Without limitation to detecting smaller or larger lesions, it is contemplated that the system 100 detects lesion sizes ranging from 5 cc-100 cc.

In some embodiments, it will not be necessary for the display 150 to show even the volume of a lesion. In those situations, the system 100 and the display 150 are adapted to show an indication of the general size of the lesion, such as small, medium, large, or extra large. Each size will have a corresponding range of volumes and possibly an associated surgical kit based on the amount of grafting material required. In such a case, the display 150 may be adapted to show a color, an appropriately sized bar, or a letter (e.g. S, M, L, or XL) corresponding to the size of the lesion. Thus, there are numerous simple visual displays that may be used to indicate the size or other data obtained by the system 100. In addition, in one embodiment the system 100 does not include a display.

In lieu of or in addition to display 150, alternative embodiments of the system include other means of outputting tissue data in human intelligible form. For example, in one embodiment the system includes an audible output, such as a speaker, adapted to provide information to the caretaker. In one embodiment, the audible output beeps or otherwise indicates the general size of the lesion or other tissue malformity. Other human intelligible forms, such as vibrations, are also contemplated as means of outputting tissue data.

In one embodiment the system may classify the size of the lesion based on a kit size related to the amount of grafting material—such as autograft, allograft, osteoconductive, or osteoinductive materials—needed to fill the lesion. For example, but without limitation, in one embodiment the void is filled with a mixture of bone morphogenic protein (BMP) carrier matrix and mineralized granules. The carrier is a collagen sponge or paste including bi-calcium phosphate. The BMP may be included in a platelet gel or may be recombinant BMP. The mineralized granules are a homogenous substance or mixture of autograft, allograft, xenograft, hydroxyl appetite, bi-calcium phosphate, coral or other materials suitable for implantation. In one aspect a small kit would be a small INFUSE® bone graft kit from Medtronic, Inc. containing a 2.5 mm collagen sponge and a vial of BMP to reconstitute in solution of 1.5 mg/ml of saline solution. A medium INFUSE® bone graft kit would contain a 5.6 mm collagen sponge and a larger vial of BMP, while a large INFUSE® bone graft kit would contain an 8.0 mm collagen sponge and a larger vial of BMP to reconstitute a solution at 1.5 mg/ml of saline solution.

As shown in FIG. 1, the hand-held device 110 is wired by cable 115 to processor 140, which in turn is connected to the display 150. This wired communication is utilized to transfer data from the hand-held device 110 to the display 150 and signal processor. In some embodiments the hand-held device 110 is adapted for wireless communication with the signal processor 140 and display 150. In this regard, the hand-held device 110 is configured to transfer data using RFID, inductive telemetry, acoustic energy, near infrared energy, "Bluetooth," or computer networks. The hand-held device 110 transfers data to offload tasks such as the computing performed by the signal processor, displaying the data, or storing the data. This is particularly true where the signal processor and the display are part of a computer system or other apparatus specifically adapted for processing, storing, and displaying the information. The hand-held device 110 also includes a memory and a port for transferring data in one embodiment. In such an embodiment, the hand-held device 110 may be utilized to obtain data and then selectively connected to the signal processor or display.

The wired communication is also utilized to provide power to the hand-held device 110. In one aspect, the hand-held device 110 receives power via a Universal Serial Bus ("USB") system. In this way the hand-held device 110 may be adapted to communicate over a USB cable with the signal processor and display so as to both receive power and transmit data. In this way, the hand-held device 100 utilizes the external device to receive power, perform the signal processing, store data, and display information. Thus, the external device may be handheld device such as a cell phone, PDA, or similar type device as well as a laptop or desktop computer.

In an alternative embodiment the hand-held device 110 is adapted to receive power from an external source dedicated solely to providing power. For example, the hand-held device 110 receives power from a wall socket or other common power source through a wired connection in some embodiments. To this end, the hand-held device 110 may itself include a wire adapted to plug into the power source. On the other hand, the hand-held device 110 may include an adapter or receiver for selectively connecting to a wired power supply, such that the instrumentation is not permanently attached to the wire. In one embodiment, the power supply of the hand-held device 110 is an internal power source. That is, the power supply is fully disposed within the hand-held device 110. In such an embodiment, the internal power source is a battery or a plurality of batteries.

It is fully contemplated that the hand-held device 110 be configured to include as few parts as needed, utilizing the features of external devices to the full extent possible. This can be very beneficial where the hand-held device 110 is adapted to be disposable such that cost is kept to a minimum. In at least one embodiment the coupling attachment 122 is disposable so that the coupling attachment is discarded after each use and the remaining portions of the hand-held device 110 and system 100 are reusable. In other embodiments the entire hand-held device 110 is disposable. That is, the hand-held device 110 is designed for use in only one medical procedure or for a limited amount of time. For example, in one aspect the hand-held device 110 includes a circuit that breaks or disconnects if the instrumentation is subjected to autoclaving or other types of sterilization procedures. The hand-held device 110 may also include a battery with a predetermined life. For example, the battery may be designed to provide power to operate the hand-held device 110 for 12 hours after initiation. This would give the hand-held device sufficient power for long surgical procedures, yet limit the useful life of the instrumentation to a single procedure.

Further, the data from the system 100 may be transmitted to an image guided surgery (IGS) system such that the data concerning the tissue properties and three-dimensional void boundaries may be integrated with the positioning data of the IGS system. Thus, a composite three-dimensional model showing the tissue type and/or void boundaries is calculated and may be displayed separately or as part of a composite image with the IGS display. The data from the system 100 may be transmitted wirelessly or by wired communication, or through a data storage device to the IGS system.

In a further embodiment, the system 100 itself is a component of an IGS system. In this embodiment, the system 100 is utilized to map the three-dimensional void boundaries and the three-dimensional location of the lesion relative to the patient's body. The IGS system then guides the user to remove all or substantially all of the lesion based on the sensed data. In an alternative embodiment, the IGS system includes an automated bone removal device in communication with the IGS system. The automated bone removal device is advanced to the lesion site under computer control, activated to remove the lesion under computer control, and removed from the lesion site. In a further embodiment, the IGS system automatically locates the lesion void after debridement and fills the void with a filler material. Finally, in another embodiment a sensor is placed in the filler material to verify complete filling of the void.

Though the system 100 has been described primarily in connection with detecting the size of lesions in bone and determining whether removal of the lesion was successful, the system according the present invention has many other applications. In one application, the system 100 is used after filling of the void with bone filling material to evaluate completeness of the filling. For example, the difference in material properties between the native bone, the bone filler and any substance left in the void can be sensed by the system 100. If a foreign substance, such as blood, air, saline solution, lesion, tumor, etc., remains after filling the void the system can detect it, display the information, and alert the user. In another application, the system 100 is configured to determine the actual density of tissue, rather than simply distinguishing between different types of tissue. This may be particularly advantageous in the treatment of patients with osteoporosis.

Although lesion has often been referred to in regards to an osteolytic lesion, lesion is intended to include any type of abnormal tissue, malformation, or wound related to a bone or other tissue, including cancers, voids, tumors, missile injuries, projectiles, puncture wounds, fractures, etc. For example, in some embodiments the disclosed system is useful to detect and determine the size of bone cancer voids, cancer cells, and tumors. Further, the system is also adapted to detect the presence of healthy tissue as well. Thus, the electronic instrumentation is adapted to determine the shape and volume of tissue features, both good and bad.

In another aspect, the system is used to remotely probe suspect tissue and alert the user to the presence of anomalous tissue based on reflected energy indicating different densities. In still a further aspect, the system is used to monitor the growth and healing of soft tissues in 3-D space, such as tendons and ligaments, as well as bone. In yet a further embodiment, the system is utilized to detect the location in 3-D space of foreign bodies, such as bullets, nails, glass, or other objects, in various types of tissue and particularly associated with penetration wounds. In one embodiment, the features of the hand-held device are combined with a grasping instrument such that the detected foreign bodies may be located, grasped by the instrument, and withdrawn from the patient.

Finally, the electronic instrumentation may be configured to perform a plurality of the various applications described above in combination. Specifically, the system may include two or more of the previously described features.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A system for providing visual feedback of a bone having an artificial implant installed therein and detecting a lesion between the bone and the artificial implant, comprising;
    a hand-held ultrasound device adapted to transmit a signal through an artificial implant to a bone, receive reflected signals indicative of a void between the implant and the bone and produce a corresponding output signal;
    a processor in communication with the hand-held ultrasound device and adapted to receive the output signal and to formulate a three dimensional image (3-D) of the void based on the output signal, wherein the processor provides a display signal of the 3-D image; and a display device configured to communicate with the processor and respond to the display signal to produce at least one 3-D image of the void on the display device.

2. The system of claim 1, wherein the processor is further configured to calculate a volumetric measurement of the void between the implant and the bone.

3. The system of claim 2, wherein the processor is configured to display the volumetric measurement of the void on the display.

4. The system of claim 1, further comprising a coupling attachment having a body formed of an ultrasonic conductive material and an inner wall defining a cavity configured to receive a portion of the ultrasound device and an outer surface configured to engage a substantial portion of the artificial implant.

5. The system of claim 4, wherein the coupling attachment is disposable.

6. The system of claim 4, wherein the artificial implant is an acetabular cup.

7. The system of claim 4, wherein the outer surface is malleable to conform to the artificial implant and the malleable portion conductively contacts the artificial implant.

8. The system of claim 4, further comprising a plurality of coupling attachments of various sizes.

9. The system of claim 1, wherein at least one of the processor and display is located in or on the hand-held ultrasound device.

10. The system of claim 1, wherein the hand-held ultrasound device communicates wirelessly with the processor.

11. A method of assessing a bone while introducing an artificial implant, the method comprising:
providing an ultrasound device, a processor and a display device;
activating the ultrasound device to produce ultrasound signals;
inserting an artificial implant;
sensing the ultrasound signals reflected from the bone through the artificial implant;
processing the reflected signals to generate at least a portion of a 3-D model of the bone; and
displaying at least a portion of the 3-D model of the lesion.

12. The method of claim 11, further including calculating a volume of a lesion in response to the reflected signals.

13. The method of claim 12, further including determining the appropriate amount of bone filler required to fill the lesion based upon the calculated volume.

14. The method of claim 11, further including debriding any lesion material detected in the bone.

15. The method of claim 14, further including after said debriding, detecting any remaining lesion material.

16. The method of claim 11, wherein prior to said activating, the user applies a first force on the area adjacent the lesion, and further including after said sensing, applying a second force different than the first force on the area adjacent the lesion, activating the ultrasound device adjacent the lesion for a second reading; and sensing a second set of reflected signals from the bone and lesion, wherein said processing includes comparing said the signals reflected from the bone and lesion under the first force with the second set of reflected signals sensed under the second force.

17. The method of claim 11, further comprising a coupling an attachment for use with the ultrasound device and the artificial implant to the ultrasound device, wherein the coupling attachment has a body formed of an ultrasonic conductive material, and the body has an internal wall defining a cavity that couples with a portion of the ultrasound device and an external surface configured to engage a substantial portion of the artificial implant.

18. The method of claim 17, wherein the artificial implant is an acetabular cup.

19. The method of claim 17, further comprising uncoupling the attachment.

20. The method of claim 17, wherein the attachment is disposable.

* * * * *